US012740932B2

(12) United States Patent
Callewaert

(10) Patent No.: US 12,740,932 B2
(45) Date of Patent: Sep. 22, 2026

(54) MICROBIAL ENZYMES TO REDUCE MALODOR OF SKIN AND TEXTILES

(71) Applicant: Phiome BV, Ghent (BE)

(72) Inventor: Chris Callewaert, Ghent (BE)

(73) Assignee: Phiome BV, Ghent (BE)

( * ) Notice: Subject to any disclaimer, the term of this patent is extended or adjusted under 35 U.S.C. 154(b) by 743 days.

(21) Appl. No.: 17/598,788

(22) PCT Filed: Mar. 30, 2020

(86) PCT No.: PCT/EP2020/058897

§ 371 (c)(1),
(2) Date: Sep. 27, 2021

(87) PCT Pub. No.: WO2020/201182

PCT Pub. Date: Oct. 8, 2020

(65) Prior Publication Data

US 2022/0168208 A1 Jun. 2, 2022

(30) Foreign Application Priority Data

Apr. 4, 2019 (EP) .................................... 19167207

(51) Int. Cl.
*A61Q 15/00* (2006.01)
*A61K 8/66* (2006.01)
*C11D 3/386* (2006.01)

(52) U.S. Cl.
CPC ................ *A61K 8/66* (2013.01); *A61Q 15/00* (2013.01); *C11D 3/386* (2013.01)

(58) Field of Classification Search
CPC ........... A61K 8/66; A61Q 15/00; C11D 3/386
See application file for complete search history.

(56) References Cited

U.S. PATENT DOCUMENTS 5,213,791 A 5/1993 Lyon et al.
5,643,559 A 7/1997 Eigen et al.
(Continued)

FOREIGN PATENT DOCUMENTS

EP 1258531 A1 11/2002
WO 91/05541 A1 5/1991
(Continued)

OTHER PUBLICATIONS

GenBank: AJP24853.1, protease [*Staphyloccus epidermidis*], published Nov. 2022 (Year: 2022).*
(Continued)

*Primary Examiner* — Thane Underdahl
*Assistant Examiner* — Mary A Crum
(74) *Attorney, Agent, or Firm* — TraskBritt

(57) ABSTRACT

The disclosure relates to the field of reducing malodor that is due to bacterial conversion of molecules that are present in sweat. This disclosure describes purified enzymes, lyophilized or non-living bacteria, bacterial lysates, and/or bacterial fragments that contain the functional potential to fully catabolize the human skin lipids and squalene, so no malodor arises. The disclosure also describes enzymes that produce a natural fragrance from squalene breakdown products. The compounds of the disclosure can, thus, be used in deodorants, washing powders, clothing finishing agents or in any method to reduce malodor.

11 Claims, 6 Drawing Sheets

(56) References Cited

U.S. PATENT DOCUMENTS

| | | | |
|---|---|---|---|
| 5,676,937 | A | 10/1997 | Eigen et al. |
| 6,951,729 | B1 | 10/2005 | Dewolf, Jr. et al. |

FOREIGN PATENT DOCUMENTS

| | | | | |
|---|---|---|---|---|
| WO | 00/01353 A1 | 1/2000 | | |
| WO | 00/01355 | 1/2000 | | |
| WO | WO-2018073278 A1 * | 4/2018 | .............. | A61K 8/99 |

OTHER PUBLICATIONS

GenBank PIH08861.1 enoyl-CoA hydratase, partial [*Staphylococcus epidermidis*], published Nov. 4, 2017 (Year: 2017).*

UniProtKB/Swiss-Prot: Q5HQ51.1, RecName: Full=Protoheme IX farnesyltransferase; AltName: Full=Heme B farnesyltransferase; AltName: Full=Heme O synthase, published Jan. 16, 2019 (Year: 2019).*

GenBank EFA87620, alpha amylase, catalytic domain protein [*Staphylococcus epidermidis* SK135], published Jun. 2013 (Year: 2013).*

GenBank AAA19729.1, lipase [*Staphylococcus epidermis*], published Jul. 1994 (Year: 1994).*

NCBI Reference Sequence: WP_080280668.1, cellulase family glycosylhydrolase [*Staphylococcus epidermidis*], published Dec. 2023) (Year: 2023).*

Hasan, Fariha, et al. "Enzymes used in detergents: lipases." African journal of biotechnology 9.31 (2010): 4836-4844. (Year: 2010).*

Barzantny, Helena, Iris Brune, and Andreas Tauch. "Molecular basis of human body odour formation: insights deduced from corynebacterial genome sequences." International journal of cosmetic science 34.1 (2012): 2-11. (Year: 2012).*

Toalá, et al. "Postbiotics: An evolving term within the functional foods field." Trends in food science & technology 75 (2018): 105-114. (Year: 2018).*

Jakoby, William B. "[23] Crystallization as a purification technique." Methods in enzymology. vol. 22. Academic Press, 1971. 248-252. (Year: 1971).*

Duong-Ly, Krisna C., and Sandra B. Gabelli. "Salting out of proteins using ammonium sulfate precipitation." Methods in enzymology. vol. 541. Academic Press, 2014. 85-94. (Year: 2014).*

Zhang, C-Y., et al. "A strategy for selecting the pH of protein solutions to enhance crystallization." Structural Biology and Crystallization Communications 69.7 (2013): 821-826. (Year: 2013).*

Callewaert et al. "Bacterial and odor profile of polyester and cotton clothes after a fitness session" Commun Agric Appl Biol Sci. 2013;78(1).

Callewaert et al. "Artificial sweat composition to grow and sustain a mixed human axillary microbiome" J Microbiol Methods. 2014;103:6-8.

Callewaert et al. "Deodorants and antiperspirants affect the axillary bacterial communitY". Arch Dermatol Res. Sep. 19, 2014;306(8):701-710.

Callewaert et al. "Towards a bacterial treatment for armpit malodour" Exp Dermatol [Internet]. Nov. 2, 20168 [cited Jan. 6, 2017]; Available from: http://www.ncbi.nlm.nih.gov/pubmed/27892611.

Hasegawa et al. "Identification of new odoriferous compounds in human axillary sweat" Chem Biodivers. 2004;1(12):2042-50.

International Search Report for International Application No. PCT/EP2020/058897, mailed Jun. 9, 2020, 4 pages.

International Written Opinion for International Application No. PCT/EP2020/058897, mailed Jun. 9, 2020, 6 pages.

Troccaz et al. "3-methyl-3-sulfanylhexan-1-ol as a major descriptor for the human axila-sweat odour profile" Chem Biodivers. (Jul. 2004), vol. 1, Issue 7, p. 1022-1035.

Daelemans et al "Recent advances in understanding and managing infantile colic" F1000Research 2018, 7(F1000 Faculty Rev): 1426 (Last updated: Sep. 7, 2018).

Pique et al "Health Benefits of Heat-Killed (Tyndallized) Probiotics: An Overview" Int J Mol Sci., 20(10):2534 May 2019); doi: 10.3390/ijms20102534.

Deshpande et al. "Para-probiotics for Preterm Neonates—The Next Frontier" Nutrients, 10(7), 871 (Jul. 5, 2018) https://doi.org/10.3390/nu10070871.

European Communication pursuant to Article 94(3) EPC for European Application No. 20714219, dated Oct. 30, 2024, 4 pages.

Holz et al. "Novel bioactive from Lactobacillus brevis DSM17250 to stimulate the growth of *Staphylococcus epidermidis*: a pilot study" Beneficial Microbes, 2017; 8(1): 121-131 (Feb. 7, 2017).

Huang et al. "Probiotics in personal care products" Microbiology Discovery, vol. 3, Article 5, pp. 1-9 (Jul. 25, 2015).

Ouwehand et al. "The Potential of Probiotics and Prebiotics for Skin Health" In: Farage, M., Miller, K., Maibach, H. (eds) Textbook of Aging Skin. Springer, Berlin, Heidelberg. https://doi.org/10.1007/978-3-662-47398-6_77 (Sep. 29, 2016).

Robles "Probiotics promising cosmetic ingredient or marketing tool?" H&PC Today, vol. 11(4) Jul./Aug. 2016.

* cited by examiner

MICROBIAL ENZYMES TO REDUCE MALODOR OF SKIN AND TEXTILES

CROSS-REFERENCE TO RELATED APPLICATIONS

This application is a national phase entry under 35 U.S.C. § 371 of International Patent Application PCT/EP2020/058897, filed Mar. 30, 2020, designating the United States of America and published as International Patent Publication WO 2020/201182 A1 on Oct. 8, 2020, which claims the benefit under Article 8 of the Patent Cooperation Treaty to European Patent Application Serial No. 19167207.0, filed Apr. 4, 2019.

TECHNICAL FIELD

The disclosure relates to the field of reducing malodor that is due to bacterial conversion of molecules that are present in sweat. This disclosure describes purified enzymes, lyophilized or non-living bacteria, bacterial lysates, and/or bacterial fragments that contain the functional potential to fully catabolize the human skin lipids and squalene, so no malodor arises. The disclosure also describes enzymes that produce a natural fragrance from squalene breakdown products. The compounds of the disclosure can, thus, be used in deodorants, washing powders, clothing finishing agents or in any method to reduce malodor.

BACKGROUND

The skin microbiome is rich and complex and every skin niche has its own specific microbiome (1). Most of the microbiota living on the skin are harmless. Some bacteria are associated with the production of malodors, while others are not associated to malodors or are even associated to good odors (2). In the case of osmidrosis, body odor, bromhidrosis, the skin microbiome is different and considered responsible for the malodor formation (3).

Treatments of axillary body odor include the use of deodorants and antiperspirants (4), botulinum toxin injections (5), axillary liposuction (6), laser- or microwave-based ablation of sweat glands (7, 8), antidepressants and antipsychotics (9), and topical antibiotics (10). Most methods focus on the sweat precipitation and not on the bacterial impact. To date, there is no lasting solution focusing against the microbiome of underarm body odor.

Deodorants and antiperspirants are widely used to mask body odor. Both use perfumes, to mask the malodor production, and generally use antimicrobial compounds, to limit the bacterial growth. Compounds with an antimicrobial and/or antifungal function that are commonly used are triclosan, triclocarsan, quaternary ammonium compounds, metal salts, aliphatic alcohols and glycols and other fragrances (11)(12). Antiperspirants generally contain aluminum salts, which blocks the sweat pores by mechanical obstruction. The ingredients with such action are aluminum chloride hexahydrate (ACH), aluminum chlorohydrate, aluminum sesquichlorohydrate, aluminum chlorohydrex and aluminum zirconium tetrachlorohydrate. The deodorants and antiperspirants of today do not adjust the microbiome. Contrary, most deodorants and antiperspirants will infer a shock to the microbial community and will lead to an increase in microbial diversity (13). This is unwanted as a higher microbial diversity is associated with a stronger underarm malodor. The abundance of corynebacteria may increase, which can lead to more malodor formation (13) (14).

The current deodorant and antiperspirants aims to reduce the microbial load, and thus also the enzymatic load.

Deodorant formulations upon today indeed target and suppress biochemical reactions that transform odor precursors into malodorous volatiles. For example, U.S. Pat. No. 5,213,791 discloses amino acid β-lyase inhibitors in deodorants. The latter document discloses this amino acid β-lyase as a malodor-forming enzyme and identifies ways to inhibit it. In other words, this document describes the inhibition of enzymes to block biochemical conversions. Also U.S. Pat. Nos. 5,676,937 and 5,643,559 describe inhibitors of bacterial sulfatases and glucuronidases, which are thought to reduce the steroidal malodor. Also here, agents to block and inhibit the enzymes responsible for biochemical conversion are disclosed. WO 00/01355 (17) further describes agents to inhibit steroid reductase and thus malodor. EP 1258531A1) (18) describes the enzyme Nα-acyl-glutamine-aminoacylase that is responsible for the release of thioalcohol-based malodor and a general formula containing ingredients to inhibit the enzyme. This enzyme can also be present in *Staphylococcus* spp., namely *S. hominis* (19), and is therefore responsible for the release of the typical oniony *sulphurous* thioalcohol-based malodor in the axillae. This document thus describes agents to inhibit the aforementioned enzyme, in order to avoid the biochemical conversion with the release of the malodorous thioalcohol as result. Similarly, U.S. Pat. No. 6,951,729B1 describes a high throughput screening method for agents affecting the enzymes involved in the fatty acid biosynthesis.

However, the use of inhibitors in deodorants and applied on skin fall short. The biochemical reaction already largely occurred in the sweat glands and the hair roots, where the deodorant ingredients cannot or can barely penetrate. The inhibitors of microbial enzymes will therefore only be partially effective.

Hence, there is still a need to find alternative products and methods that are useful to combat malodor.

BRIEF SUMMARY

Contrary to the inhibition of enzymes, the use of enzymes to foster or encourage the biochemical conversion of sweat precursors has not been disclosed before.

The disclosure describes the addition of extra enzymes to fully convert the biochemical compounds in, as an example, the underarm. This disclosure does not thus describe the inhibition of microbial enzymes. In contrast, the disclosure adds extra active enzymes to selectively steer the biochemical reaction towards the release of non-odorous volatiles. By promoting one biochemical reaction, we selectively create breakdown of sweat molecules that are not odorous, and avoid the biochemical breakdown of sweat molecules by the armpit microbiome into malodorous molecules.

In one aspect, the disclosure describes the use of fatty acid-degrading enzymes to enable fatty acid breakdown and sweat molecules on skin and clothes to encourage the complete breakdown of fatty acids release from sebaceous and apocrine sweat glands.

The disclosure also further describes the use of enzymes to fully catabolize squalene and biochemically break it down towards non-malodorous molecules or useful building blocks. The disclosure further describes a series of enzymes that use squalene and converts it into farnesyl, mevalonate and acetyl. In other words, the present disclosure describes the usage of enzymes to convert naturally secreted molecules on skin to produce other useful compounds on skin, rather than degrading and producing malodorous volatiles.

As indicated above, the current deodorants and antiperspirants aims to reduce the microbial load, and thus also to reduce the enzymatic load. In contrast, the disclosure describes adding extra enzymes to deodorants and antiperspirants in order to help the biochemical breakdown of sweat secretions. Indeed with the addition of extra enzymes, the disclosure describes dissolving the sweat secretions and lipids into small compounds that do not have a bad odor.

In fact, the disclosure relates to the finding that enzymes from *Staphylococcus epidermidis* have the ability to fully convert lipids secreted on the skin whereas Corynebacteria and other malodor-associated bacteria lack the ability the fully catabolize the lipids. This is in contrast with the prior art wherein it is indicated that Corynebacteria contain a rich set of enzymes and that *Corynebacterium* spp. predominantly feed on skin secretions containing a variety of different lipid compounds (21). It is further indicated that to compensate for its incapability in synthesizing fatty acids, *Corynebacterium* spp. harbor a comprehensive set of enzymes involved in lipid metabolism encoded by multiple paralogous genes (22, 23). This feature enables the organism to metabolize a broader range of lipid compounds (24). In contrast, the present disclosure shows that *Staphylococcus epidermidis* has a broader set of lipolytic enzymes than *Corynebacterium* spp. In addition, the present disclosure describes that *Staphylococcus epidermidis* also has a broader set of squalene-degrading enzymes. Squalene can convert into steroids that can be biochemically broken down and can cause malodor (25).

The disclosure thus describes the usage of purified enzymes, bacterial fragments, dead or viable lyophilized bacteria, and/or bacterial lysates to combat skin malodor. The enzymes will fully catabolize skin lipids and squalene so that no malodor is generated. The enzymes may originate from *Staphylococcus* spp., and more in particular from *Staphylococcus epidermidis*.

Lyophilization refers to the process in which bacteria are cultured and preserved by freezing very quickly and subsequently subjecting to a vacuum to remove the ice. Lyophilization is one of the most effective methods for the long-term preservation of cells. Freeze drying, known as lyophilization, is used to prepare bacterial culture that can be revived upon contact with moisture (26).

Hence, the disclosure relates to the usage of lipolytic enzymes obtained from a bacterial *Staphylococcus* species to reduce the amount of malodorous short-chain fatty acids released from unusual, methyl-branched, odd-numbered long-chain fatty acids present in sweat. The human fatty acids present on the stratum corneum are often called “unusual,” as no other animal contains such mixture of methyl-branched and odd-numbered fatty acids on the skin.

Fatty acids of the human skin consists of saturated fatty acids, among which and not limited to palmitic acid (C16), myristic acid (C14), stearic acid (C18), pentadecanoic acid (C15), heptadecanoic acid (C17); unsaturated fatty acids, among which and not limited to cis-hexadec-6-enoic acid (16:1 Ω6), cis-octadec-8-enoic acid (18:1 Ω8), oleic acid (18:1 Ω9), petroselenic acid (18:1 Ω6), cis-heptadec-6-enoic acid (17:1 Ω6), cis-tetradec-6-enoic acid (14:1 Ω6), sebaleic acid (18:2 Ω5,8), cis-heptadec-8-enoic acid (17:1 Ω8), linoleic acid (18:2 Ω9,12), cis-eicos-10-enoic acid (20:1 Ω10), cis-eicos-7,10-dienoic acid (20:2 Ω7,10); iso-branched fatty acids, among which and not limited to 4-methyltetradecanoic acid, cis-14-methylpentadec-6-enoic acid, cis-16-methylheptadec-8-enoic acid; anti-iso-branched fatty acids, among which and not limited to 12-methyltetradecanoic acid, cis-14-methylhexadec-6-enoic acid (21, 27, 28).

Malodorous short-chain fatty acids or “malodorous fatty acids” are defined as, but not limited to, 3-methyl-2-hexenoic acid (3M2H), 3-hydroxy-3-methylhexanoic acid (HMHA) (29-31), 3-methyl-3-octenoic acid, 4-methyl-3-nonenoic acid, 3-hydroxy-4-methylhexanoic acid, 3-hydroxy-3-methylheptanoic acid, 3-hydroxy-4-heptanoic acid, 3-hydroxyoctanoic acid, 3-hydroxy-3-methyloctanoic acid, 3-hydroxy-4-methyloctanoic acid, 3-hydroxy-4-methylnonacoic acid, 3-hydroxydecanoic acid (31), isovaleric acid (32), 4-ethyloctanoic acid, 7-octenoic acid (29), 1-octen-3-ol, 1,5-octadien-3-one (33). Thorough reviews on the topic of short-chain fatty acids and other malodorants derived from human sweat can be found in Takeuchi et al. (33) and Martin et al. (34).

The disclosure thus relates to the usage of lipolytic or squalene-degrading enzymes obtained from a bacterial *Staphylococcus* species to reduce the amount of malodorous fatty acids, preferably short-chain fatty acids, in sweat.

This disclosure further relates to the usage of lipolytic or squalene-degrading enzymes as described above wherein the *Staphylococcus* species is *Staphylococcus epidermidis.*

The disclosure also relates to the usage of lipolytic or squalene-degrading enzymes as described above wherein the enzymes are administered as purified enzymes or as part of a bacterial fragment, dead bacterium or bacterial lysate or a viable lyophilized bacterium.

This disclosure relates to the usage of lipolytic enzymes as described above wherein the enzymes are part of the beta-oxidation pathway or the fatty acid biosynthesis pathway or the synthesis and degradation of ketone bodies pathway or terpenoid backbone biosynthesis pathway or steroid biosynthesis pathway of a bacterial *Staphylococcus* species.

The disclosure further relates to the usage of lipolytic enzymes as described above wherein the lipolytic enzymes that are part of the beta-oxidation pathway (or fatty acid degradation pathway) are chosen from the list consisting of: FadE (acyl CoA dehydrogenase), FadB (enoyl CoA hydratase), FadJ (3-hydroxyacyl-CoA dehydrogenase), FadA (β-ketothiolase).

This disclosure also relates to the usage of lipolytic enzymes as described above wherein the lipolytic enzymes that are part of the fatty acid biosynthesis pathway are chosen from the list consisting of: AccA (acetyl-CoA carboxylase), AccB (acetyl-CoA carboxylase), AccC (acetyl-CoA carboxylase), AccD (acetyl-CoA carboxylase), FabD (malonyl-CoA:ACP transacylase), FabH (β-ketoacyl-ACP synthases), FabG (NADPH-dependent β-ketoacyl-ACP reductase), FabZ (3-hydroxyacyl-ACP dehydratase), FabA (β-hydroxydecanoyl-ACP dehydrase), FabB (3-ketoacyl-ACP synthases I), FabF (β-ketoacyl-ACP synthase (chain elongation)), FabI (enoyl-ACP reductase), FabL (enoyl-ACP reductase) and FabK (enoyl-ACP reductase).

The disclosure further relates to the usage of lipolytic enzymes as described above wherein the enzymes that are part of the synthesis and degradation of ketone bodies are chosen from the list consisting of: acetyl-CoA C-acetyltransferase, hydroxymethylglutaryl-CoA synthase, hydroxymethylglutaryl-CoA lyase, 3-oxoacid CoA-transferase, acetoacetate decarboxylase, 3-hydroxybutyrate dehydrogenase.

This disclosure also relates to the usage of squalene-degrading enzymes as describe above, wherein the squalene-degrading enzymes are chosen from the list consisting of: farnesyl-diphosphate farnesyltransferase, farnesyl diphosphate synthase, diphosphomevalonate decarboxylase, phosphomevalonate kinase, mevalonate kinase, hydroxymethylglutaryl-CoA reductase, hydroxymethylglutaryl-CoA synthase, acetyl-CoA C-acetyltransferase. Through usage of the enzymes indicated above, the breakdown products of the lipid and squalene metabolism can be further used into the metabolism of bacteria or bacterial cell mass. Indeed, the present disclosure relates to the usage of squalene catabolizing enzymes to degrade to building blocks such as farnesyl, mevalonate and acetyl. Through the use of the enzymes, squalene is completely broken down, and no longer converted to steroids and can no longer lead to malodorous compounds.

This disclosure further relates to the usage of lipolytic enzymes or squalene-degrading enzymes as described above wherein lipases, amylases, proteases and/or cellulases that are obtained from any microbial species are further added to the lipolytic or squalene-degrading enzymes.

The disclosure also relates to the usage of lipolytic or squalene-degrading enzymes as described above wherein the sweat is present on skin and/or textiles.

In addition, this disclosure relates to the usage of farnesyl diphosphatase to produce a natural fragrance on skin.

Moreover, the present disclosure relates to the usage of farnesyl diphosphatase as described above, wherein the farnesyl diphosphatase is obtained from a *Saccharomyces* species.

This disclosure relates to the usage of farnesyl diphosphatase as described above, wherein the *Saccharomyces* species is *Saccharomyces cerevisiae.*

Indeed, the disclosure relates to the usage of farnesyl diphosphatase to convert farnesyl-PP to farnesol and farnesal, which have natural perfuming properties. Farnesyl-PP is a breakdown product from squalene. Through this enzyme, naturally present in *Saccharomyces*, the intermediate compound is converted to a natural perfume. Converting these intermediates into perfuming agents also prevents the breakdown into malodorous compounds.

DETAILED DESCRIPTION

Figure 1:
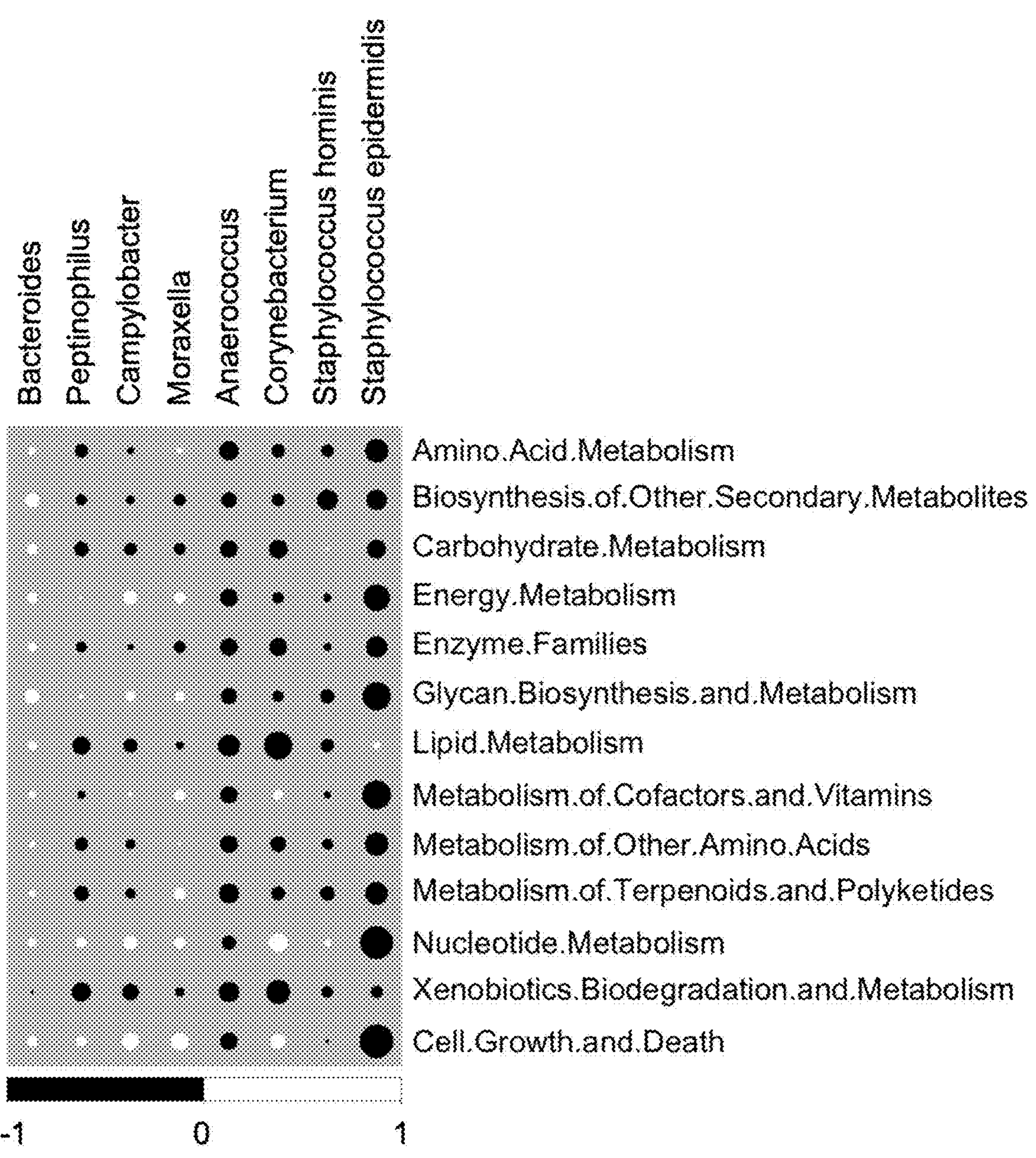
FIG. 1: Metagenome prediction collapsed to level 2 correlation plot with most important axillary taxa of the armpit observation study. A black color means a low enzymatic load; a white color refers to a higher enzymatic load. The genetic content is divided into classes such as lipid metabolism, energy metabolism, etc. Enzyme families collapsed to level 2 of KEGG pathways.

This disclosure relates to the following enzymes that fully catabolize sweat secretions into non malodorous side-products. The enzymes are part of the fatty acid degradation and fatty acid biosynthesis pathways: FadE (acyl CoA dehydrogenase), FadB (enoyl CoA hydratase), FadJ (3-hydroxyacyl-CoA dehydrogenase), FadA (β-ketothiolase), AccA (acetyl-CoA carboxylase), AccB (acetyl-CoA carboxylase), AccC (acetyl-CoA carboxylase), AccD (acetyl-CoA carboxylase), FabD (malonyl-CoA:ACP transacylase), FabH (β-ketoacyl-ACP synthases—initial condensation with acetyl-CoA and branched acyl-CoAs), FabG (NADPH-dependent β-ketoacyl-ACP reductase), FabZ (3-hydroxyacyl-ACP dehydratase), *FabA* (β-hydroxydecanoyl-ACP dehydrase), FabB (3-ketoacyl-ACP synthases I), FabF (β-ketoacyl-ACP synthase (chain elongation)), FabI (enoyl-ACP reductase), FabL (enoyl-ACP reductase) and FabK (enoyl-ACP reductase).

More specifically, the disclosure relates to the following enzymes that are part of the KEGG synthesis and degradation of ketone bodies (and use acetyl-CoA for further uptake into bacterial metabolism): acetyl-CoA C-acetyltransferase, hydroxymethylglutaryl-CoA synthase, hydroxymethylglutaryl-CoA lyase, 3-oxoacid CoA-transferase, acetoacetate decarboxylase, 3-hydroxybutyrate dehydrogenase. Through usage of these enzymes, the breakdown products of the lipid and squalene metabolism can be further used into the metabolism of bacteria or bacterial cell mass.

This disclosure further relates to the usage of lipolytic enzymes as described above wherein lipases, amylases, proteases and/or cellulases that are obtained from any microbial species are further added to the lipolytic enzymes.

More specifically, the disclosure relates to the following enzymes that degrade squalene into smaller non-odorous compounds: farnesyl-diphosphate farnesyltransferase, farnesyl diphosphate synthase, diphosphomevalonate decarboxylase, phosphomevalonate kinase, mevalonate kinase, hydroxymethylglutaryl-CoA reductase, hydroxymethylglutaryl-CoA synthase, acetyl-CoA C-acetyltransferase. The usage of squalene catabolizing enzymes promotes the conversion into useful building blocks for microbial biomass, non-malodorous molecules or even good odorous molecules, such as farnesyl, mevalonate and acetyl. Through the use of the enzymes, squalene is completely broken down, and no longer converted to steroids and can no longer lead to malodorous compounds. These enzymes are naturally present in *Staphylococcus* spp. and can be obtained and purified from their cells.

This disclosure further relates to the usage of lipolytic and squalene-degrading enzymes as described above wherein farnesyl-diphosphate, which is obtained from a *Saccharomyces* species, is further added to the enzymes. Farnesyl diphosphatase converts farnesyl-PP to farnesol and farnesal, which have natural perfuming properties. Farnesyl-PP is a breakdown product from squalene. Through this enzyme, highly present in *Saccharomyces*, the intermediate compound is converted to a natural perfume. Converting these intermediates into perfuming agents also prevents the breakdown into malodorous compounds.

Detailed information about the above-described enzymes can, for example, be found in Fujita et al. (2007) (35).

The disclosure thus relates in a first instance to compositions that degrade lipids and/or fatty acids secreted by the skin into smaller compounds that do not have a bad smell. The composition can be enzymes and/or bacterial lysates and/or inactive bacteria and/or lyophilized bacteria that have the enzymatic potential to catabolize the precursors that normally lead to underarm malodor into molecules that no longer smell bad. The enzymes and/or bacterial lysates and/or inactive bacteria (i.e., bacterial fragment and or dead bacteria) and/or living or lyophilized bacteria of the present disclosure can be obtained by any manner known in the art and/or as specified further in the examples.

Underarm malodor is characterized by a sour, musty, sharp, oniony and/or fecal-like smell. The enzymes described in this disclosure can convert the precursor and/or intermediate breakdown products into molecules that no longer have the above-described odor.

(1) Typical human, methyl-branched, odd-numbered long-chain fatty acids (LCFA) are degraded via β-oxidation into short-chain, volatile fatty acids (36, 37).

(2) Additionally, the release of short-chain fatty acids, such as E-3-methyl-2-hexenoic acid (3M2H), 3-hydroxy-3-methyl-hexanoic acid (HMHA), and a wide range of other structurally unusual VFAs, secreted as L-glutamine conjugates in apocrine glands, are considered as major components of the axillary malodor (29-31). After secretion by apocrine sweat glands, bacteria remove the L-glutamine residue with $N^{\alpha}$-acyl-glutamine aminoacylase and consequently releasing the VFAs.

(3) Several thioalcohols, such as 3-methyl-3-sulfanylhexan-1-ol (3M3SH) and 2-methyl-3-sulphanylbutan-1-ol (2M3SB), as well as their isomers were also reported as important contributors to axillary malodor (38-40).

(4) The biotransformation of steroids. Steroids secreted in the underarm through the apocrine glands secrete a series of steroids, through the ABCC11 gene (41). The bacterial breakdown products, although not fully characterized, are known to cause a specific malodor (25).

This disclosure relates to methods that mainly impacts the first and second route to malodor. The present disclosure does not relate to the inhibition of specific enzymes that cleave off L-glutamine residues or cysteine residues from malodor precursors.

The disclosure reduces the formation of malodorous (short-chain) fatty acids (released from human methyl-branched, odd-numbered long-chain fatty acids). The long-chain fatty acids present in human sweat, released from sebaceous and apocrine sweat, is, as disclosed herein, completely broken down into ATP and building blocks for bacterial de novo fatty acid synthesis. The pathways leading to malodor are converted towards pathways that no longer cause malodorous volatiles. The fatty acids are fully catabolized by the administered enzymes, when applied in an effective amount of a composition as defined above to a mammal in need thereof.

EXAMPLES

1. Materials and Methods

1.1 Armpit Observation Study: Underarm Microbiome Analysis of 189 People

1.1.1 Subjects

Triplicate bacterial samples were taken from the axillary skin of 189 healthy subjects. Sample demographic characteristics can be found in Table 1. Subjects younger than 18 years were accompanied by a parent. All participants were Belgian, except two participants from The Netherlands and one from France. Samples were collected on three different days spread over a period of six weeks. The participants were invited to Ghent and were asked not to use deodorants or antiperspirants three days prior to sampling and not to wash their axillae on the day of sampling. No attempts were made to control the subjects' diet. All participants were asked to fill in their personal metadata and a questionnaire regarding the effect of the malodor on their daily lives. All participants attached a sterile cotton pad under their left axilla for 3 hours for odor assessment. All participants gave their written and informed consent to this research.

TABLE 1

Sample demographic characteristics of the armpit screening study.

| | Total | M | F |
|---|---|---|---|
| N | 189 | 62 | 127 |
| Age | | | |
| 14-24 | 48 | 9 | 39 |
| 25-34 | 51 | 14 | 37 |
| 35-44 | 29 | 12 | 17 |
| 45-54 | 32 | 11 | 21 |
| 55-64 | 19 | 10 | 9 |
| 65+ | 8 | 6 | 2 |
| BMI | | | |
| <20 | 14 | 1 | 13 |
| 20-25 | 101 | 31 | 70 |
| 25-30 | 53 | 21 | 32 |
| >30 | 19 | 8 | 11 |
| Nationality | | | |
| Belgian | 186 | 61 | 125 |
| The Netherlands | 2 | 0 | 2 |
| France | 1 | 1 | 0 |

TABLE 1-continued

Sample demographic characteristics of the armpit screening study.

| | Total | M | F |
|---|---|---|---|
| Ethnicity | | | |
| Caucasian | 184 | 62 | 122 |
| Asian | 2 | 0 | 2 |
| Black | 3 | 0 | 3 |

1.1.2 Sampling

A sterile cotton swab (Biolab, Belgium) was moistened in physiological water and swabbed for 15 seconds in the axillary region to detach and absorb the microorganisms. The tip was suspended and broken in a sterilized reaction tube filled with 1 ml of sterile physiological water (42). The bacterial samples were immediately stored at 4° C. not longer than 48 hours prior to further analysis. The participants attached a sterile cotton pad with a dressing under their left axilla for 3 hours to absorb the odor. Afterwards, the cotton pad was brought into a closed numbered goblet until odor assessment by an odor panel.

1.1.3 Odor Assessment

The odor panel was trained and selected and samples were rated as previously described (43). Odor measurement was performed by means of a cotton pad worn in the axilla for 3 hours. The cotton pads were presented in a numbered odorless sealed glass goblet in a random manner to a panel of six selected and screened human assessors (four men, four women). Assessors were selected by means of sensitivity to dilutions of n-butanol and wastewater, and by means of the triangle test (44). In the triangle test, each member of the panel was presented three flasks, two of which were the same but the third contained a different odor. The flask was shaken, the stopper was removed, after which the vapors were evaluated. The panelists had to correctly identify the flask with the different odor. In the dilution test, each member of the panel was presented six flasks with increasing concentration of n-butanol and wastewater, starting with a flask without addition of n-butanol or wastewater. The panelists had to correctly place the flasks according concentration. The triangle and dilution test was repeated three times, with a minimum of two days in between each measurement. Assessors with minimum 85% correct answers were selected for the panel. A representative panel was recruited from a pool of the 20 people. Training of the assessors was conducted through odor references (ammonia, cheese, axillary sample) and experience. The references were assessed in group to compromise hedonic value and intensity. The room in which the tests were conducted, was free from extraneous odor stimuli, e.g., caused by smoking, eating, soaps, perfume, etc. The odor assessors were familiar with the olfactometric procedures and met the following conditions: (i) older than 16 years and willing to follow the instructions; (ii) no smoking, eating, drinking (except water) or using chewing gum or sweets 30 minutes before olfactometric measurement; (iii) free from colds, allergies or other infections; (iv) no interference by perfumes, deodorants, body lotions, cosmetics or personal body odor; (v) no communication during odor assessment. About 60 odor measurements were performed per day, spread over a timeframe of 4 hours, to prevent fatigue. The samples of the observational study were assessed by the following odor characteristic: intensity (scale 0 to 10). The intensity indicates the quantity of the odor and varies between 0 (no odor) to 10 (very strong/intolerable). Each time, a control odor measurement, a clean cotton pad with random number, was served to the odor panel together with the other samples. Odor assessment was in the observational study additionally performed via direct odor assessment (first 60 participants), and a self-evaluation (all participants).

1.1.4 DNA Extraction, PCR

Total DNA extraction was performed as previously described (45). Briefly, the bacterial sample, dissolved in 1 ml of saline water, was centrifuged (12 minutes, 13,000 rpm) to obtain a pellet, while the supernatant was discarded. The pellet was washed and resuspended in 100 μL 6% Chelex 100 resin (BioRad, Munich, Germany) and incubated at 56° C. for 20 minutes. The removal of PCR inhibitors and metal ions was accomplished by means of Chelex-100. The sample was then firmly vortexed and boiled at 100° C. for 8 minutes. Subsequently, the sample was mixed and cooled for 5 minutes on ice. Next, a centrifugation step (10 minutes, 13,000 rpm) was performed. The supernatant containing the DNA was removed and stored at −20° C. until further analysis.

The polymerase chain reaction (PCR) is a technique to amplify a piece of DNA, generating millions of copies of a particular DNA sequence. This method consists of repeated cycles of heating and cooling, which promotes the melting and separation of the double-stranded DNA. A target region of interest in the 16S rRNA bacterial gene is selected as a marker for thermal cycling, consisting of the reaction for DNA melting and enzymatic replication of the DNA. At present, the bacterial ribosomal RNA operon, encompassing the 16S rRNA gene, is the most frequently used molecular marker. The bacterial ribosomal RNA operon, encompassing the 16S rRNA gene, is the most frequently used molecular marker. The hypervariable regions of the gene (V regions) has a high discriminatory potential (46) and contains the signatures of phylogenetic groups and even species. It enables an accurate description of the microbial populations in a community (47). Therefore, molecular techniques based on 16S rDNA can be useful tools to gain insight on phylogenetic and functional relationships among the microbiota of any given environment. Two primers were used to amplify a target region of the 16S rRNA gene. As PCR progresses, the sequences generated are used as a template for replication and exponentially amplified with each cycle.

1.1.5 Illumina MiSeq Sequencing

Genomic DNA axillary samples from 189 participants were amplified with conserved 16S rRNA gene primers generating 140-bp amplicons. The 16S rRNA gene regions were amplified by PCR using the 27F and 338R primers, targeting the V1 region and libraries for Illumina sequencing were constructed as previously described (48). Briefly, the forward primer contains a 6 nucleotide (nt) barcode45 and a 2 nt CA linker (49). Both primers comprised sequences complementary to the Illumina specific adaptors to the 5'-ends. Amplification was performed in a total volume of 50 μL with 5× PrimeSTAR buffer, containing 2.5 mM deoxynucleoside triphosphate, 0.2 μM of each primer, 1 μL template DNA and 0.5 μL PrimeSTAR HS DNA polymerase (2.5 U). PCR was performed with the following conditions: initial denaturation (95° C.—3 minutes), followed by 15 cycles of denaturation, annealing and elongation (98° C.—10 seconds; 55° C.—10 seconds and 72° C.—45 seconds). One μL of this reaction mixture served as template in a second PCR performed under the same conditions, but for 20 cycles using PCR primers designed to integrate the sequence of the specific Illumina multiplexing sequencing primers and index primers. PCR amplicons were verified by agarose gel electrophoresis, purified using Macherey-Nagel 96-well plate purification kits (Macherey-Nagel, Germany) following the manufacturer's instructions and quantified with the Quant-iT PicoGreen dsDNA reagent and kit (Invitrogen, UK). Libraries were prepared by pooling equimolar ratios of amplicons (200 ng of each sample), all tagged with a unique barcode. Each library was precipitated on ice for 30 minutes after addition of 20 μl of 3M NaCl and 3 volumes of ice-cold 100% ethanol to remove contaminants or PCR artefacts. The precipitated DNA was centrifuged at 13,000×g for 30 minutes at 4° C. The supernatant was removed, the pellet air dried, resuspended in 30 μL of double-distilled water and separated on a 2% agarose gel. PCR products of the correct size were extracted and recovered using the QIAquick gel extraction kit (Qiagen, Belgium). Negative controls (water as template) were performed and were free of any amplification products after PCR. Libraries were sent for paired-end sequencing on a MiSeq Genome Analyzer (Illumina Inc., California, USA). Image analysis and base calling were accomplished using the Illumina Pipeline (version 1.7).

1.1.6 Downstream Analysis, Taxonomy, Alpha- and Beta-Analysis

Demultiplexed and quality-controlled sequences were clustered against the Greengenes (50) database using the closed reference OTU picking protocol (51) as implemented in QIIME1.9.0 (52). These processing steps were performed using default parameters. The OTU table used for primary analysis was filtered. Finally, the table was rarefied to normalize for sample effort at 1000 sequences per sample (53). Taxonomy was determined and alpha- and beta-diversity calculations were performed using QIIME version 1.9.1.

1.1.7 Metagenome Analysis

Indications of functionality from phylogenetic information was obtained with PICRUSt (54). The open-source software allows reconstruction of the bacterial metagenomes of the obtained results based on the bacterial 16S rRNA gene sequence. The generated OTU table from the 16S sequencing data was used as an input. The copy number per OTU was normalized before the metagenome was predicted using Kyoto Encyclopedia of Genes and Genomes (KEGG) database (55). The metagenome prediction provided an annotated table of predicted gene family counts for each sample, where gene families were grouped by KEGG Orthology (KO) identifiers (FIG. 1).

1.1.8 Production of Bacteria

The bacterial cells are grown to late log or early stationary phase for about 18 hours in LB medium until an $OD_{600}$ of about 0.8. The cells are harvested by centrifugation (6000 rpm/5 minutes), after which the supernatant is discarded. The cells are washed in sterile M9 medium. To create 1 L of M9 medium, one needs at first a salt solution (1 L) that consists of: 42 g $Na_2HPO_4 \cdot 7H_2O$, 15 g $KH_2PO_4$, 2.5 g NaCl, 5 g $NH_4Cl$. All compounds are added to a Schott bottle of 1 L, which is diluted with distilled water until one reaches 1 L. This solution is autoclaved prior to use. Again, the cells are harvested by centrifugation; after which the supernatant is discarded. The bacterial biomass is suspended in an equal volume of lyophilization medium. The lyophilization medium contains suitable lyoprotectants and excipients, preferably sucrose and mannitol. The mixture is mixed thoroughly by vortexing. The cell suspension is distributed over a flat surface prior to freezing. The cell suspension is kick-frozen in −80° C. in liquid nitrogen prior to the eventual freeze-drying. The frozen suspension is freeze dried and lyophilized (under vacuum pressure). A cell count is performed after the freeze-drying protocol (dilution to extinction protocol). The final concentration should be around $10^{12}$ CFU/g.

1.1.9 Production of Bacterial Enzymes or Lysates

The bacterial culture is grown for 18 hours in LB medium until an $OD_{600}$ of about 0.8; until the bacteria are in plateau phase. The cells are harvested by centrifugation (6000 rpm/5 minutes), after which the supernatant is discarded. The dense culture (pellet) is frozen at −80° C. About 1.5 ml of the pellet is resuspended in 0.75 ml lysis buffer. The lysis buffer contains 50 mM Tris pH 8.0; 10% glycerol; 0.1% Triton X-100; 100 ug/ml lysozyme; 1 mM PMSF and/or more anti-proteases; DNAse 3 U and 2 mM MgCl on the final concentration. The pellet and lysis buffer are incubated on 30° C. for 15 minutes or 30 minutes on ice. The resulting solution is sonicated 3×20 minutes until sample is no longer viscous. Ultrasonication at frequencies around 20 kHz was used to kill bacteria and to release their enzymatic contents. It was for many years has been standard technique in microbiology for the disruption of living cells (56). The solution is subsequently centrifuged at 12,000 rpm for 20 minutes at 4° C. The solution is transferred to new tubes and re-suspended in 0.75 ml lysis buffer. Then 60 ul of the solution is centrifuged, after which 20 μl 4× sample buffer with 100 mM DTT. The rest of the lysates is frozen in −20° C. A cell count is performed after the lysis protocol (dilution to extinction protocol). The final concentration should be 0 CFU/g.

1.1.10 Production of Purified Enzymes

Staphylococcal enzymes were produced as follows: 1) sonication to disrupt the bacterial cells (57) as described before, 2) centrifugation to separate the large particles from the enzymes, 3) bringing it in solution, 4) purification and precipitation of proteins (enzymes) using ammonium sulphate and crystallization by changing the pH (58).

1.1.11 Enzymatic Tests

The activity of the enzymes of the bacterial lysates and the purified enzymes was verified using a turbidity assay. We tested for the ability to degrade lipids using a turbidity assessment assay as adopted from Lawrence et al. (59), and further modifications (60). Human lipids, as obtained from liposuction and as described earlier (61), were emulsified in agar and poured into Petri dishes. The agar consistency was very turbid as a result of the lipids in the agar. The bacterial lysates and purified enzymes were brought onto the solid agar in droplets. Hydrolysis of the lipid emulsion was observed by formation of a zone of clearance around the droplet. Lipophilic enzyme activity was measured by the clearing zone on and around the droplet. Degradation of dense human lipids and conversion into different compounds led to a change in turbidity. A positive control with living bacteria and a negative control using no bacteria or enzymes was also assessed.

1.1.12 Study Design Sprays with Lyophilized Bacteria or Bacterial Enzymes

A spray was assembled using living lyophilized bacteria, inactive/dead bacterial lysates containing viable enzymes and the purified enzymes. Subjects were selected with above-average malodorous axillae (Table 1), as determined by the odor panel and six subjects were recruited (section 1.1.3). A one-month follow-up was scheduled, where the underarm odor was measured every week. A spray was prepared containing the live bacteria, the bacterial lysates/purified enzymes. This spray was used on a daily basis (once or twice application per day).

1.2 In Vivo Experiments 1.2.1 Spray Experiment with Lyophilized Bacteria

Subjects with malodorous axillae were recruited to conduct an experiment, where they applied a spray solution containing lyophilized *S. epidermidis* bacteria. The content of the spray was as follows:

2.00 g *S. epidermidis* lyophilized 50-200 um
8.00 g cyclopentasiloxane
0.20 g isopropyl myristate
0.20 g stearalkonium hectorite
0.10 g propylene carbonate
40.00 g butane, propane, isobutane pre-mix
100 ml spray bottle, under pressure It was tested and verified on agar plate that the final concentration of bacteria with one normal spray is about $10^8$ CFU/spray. The subject's underarm odor was assessed, as described above (1.1.3), before, during and after application of the spray. The subject applied the spray on a daily basis during four consecutive weeks, where the armpit was sampled every week during that period.

1.2.2 Spray Experiment with Bacterial Enzymes

Ultrasonication at frequencies around 20 kHz was used to kill bacteria and to release their enzymatic contents. It was for many years has been standard technique in microbiology for the disruption of living cells (56). A spray was created containing the non-viable *S. epidermidis* bacterial lysates, containing active enzymes. Other enzymes, such as lipases, amylases, proteases, cellulases, farnesyl-diphosphate, were purchased through normal commercial canals: Christian Hansen, Denmark; Novozymes, Denmark; DuPont, USA; Lallemand, France; or DSM, The Netherlands. The enzymes were either obtained as purified enzymes or as microbial lysate. The content of the spray was similar as before:

2.00 g ultrasonicated *S. epidermidis* lysates containing active enzymes
0.20 g lipases, amylases, proteases, cellulases, farnesyl-diphosphate
8.00 g cyclopentasiloxane
0.20 g isopropyl myristate
0.20 g stearalkonium hectorite
0.10 g propylene carbonate
40.00 g butane, propane, isobutane pre-mix
100 ml spray bottle, under pressure The subject's underarm odor was assessed, as described above (1.1.3), before, during and after application of the spray. The subject applied the spray on a daily basis during four consecutive weeks, where the armpit was sampled every week during that period.

2. Results 2.1 Screening of Underarms

Figure 2:
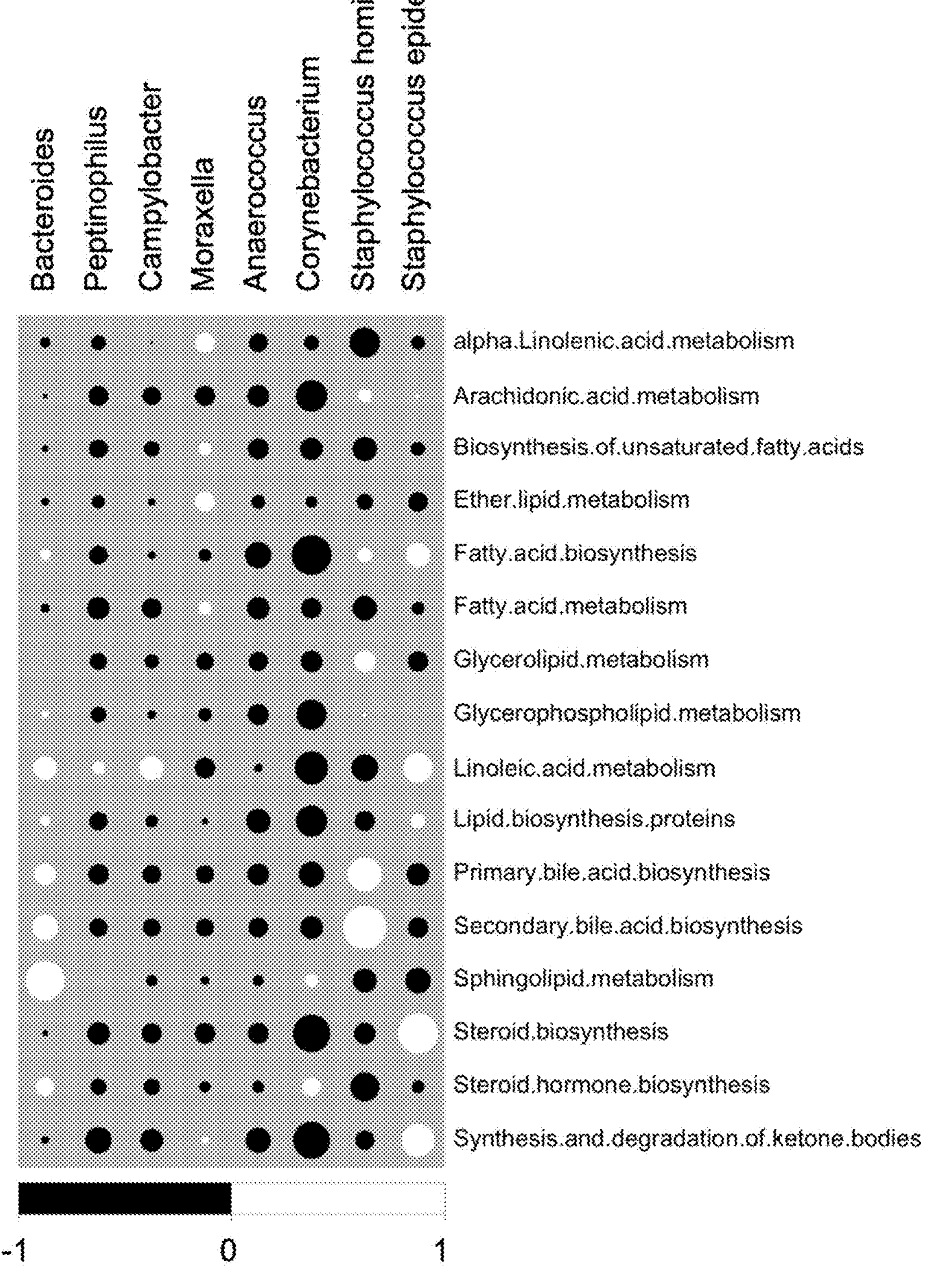
FIG. 2: Correlations between KEGG bacterial predicted metabolic fat metabolism pathways (from PICRUSt) and bacterial abundances. The most odor-contributing and high abundant underarm genera are presented. KEGG metabolic pathways are only presented for fat-metabolizing enzymes. The color of bubble, along with size, is indicative of the Kendall rank correlation coefficient between matrices. White designates a positive correlation while black designates a negative correlation. *Staphylococcus* has a positive correlation for fatty acid biosynthesis, and thus has a higher abundance of enzymes to utilize fatty acids breakdown products.
Figure 3:
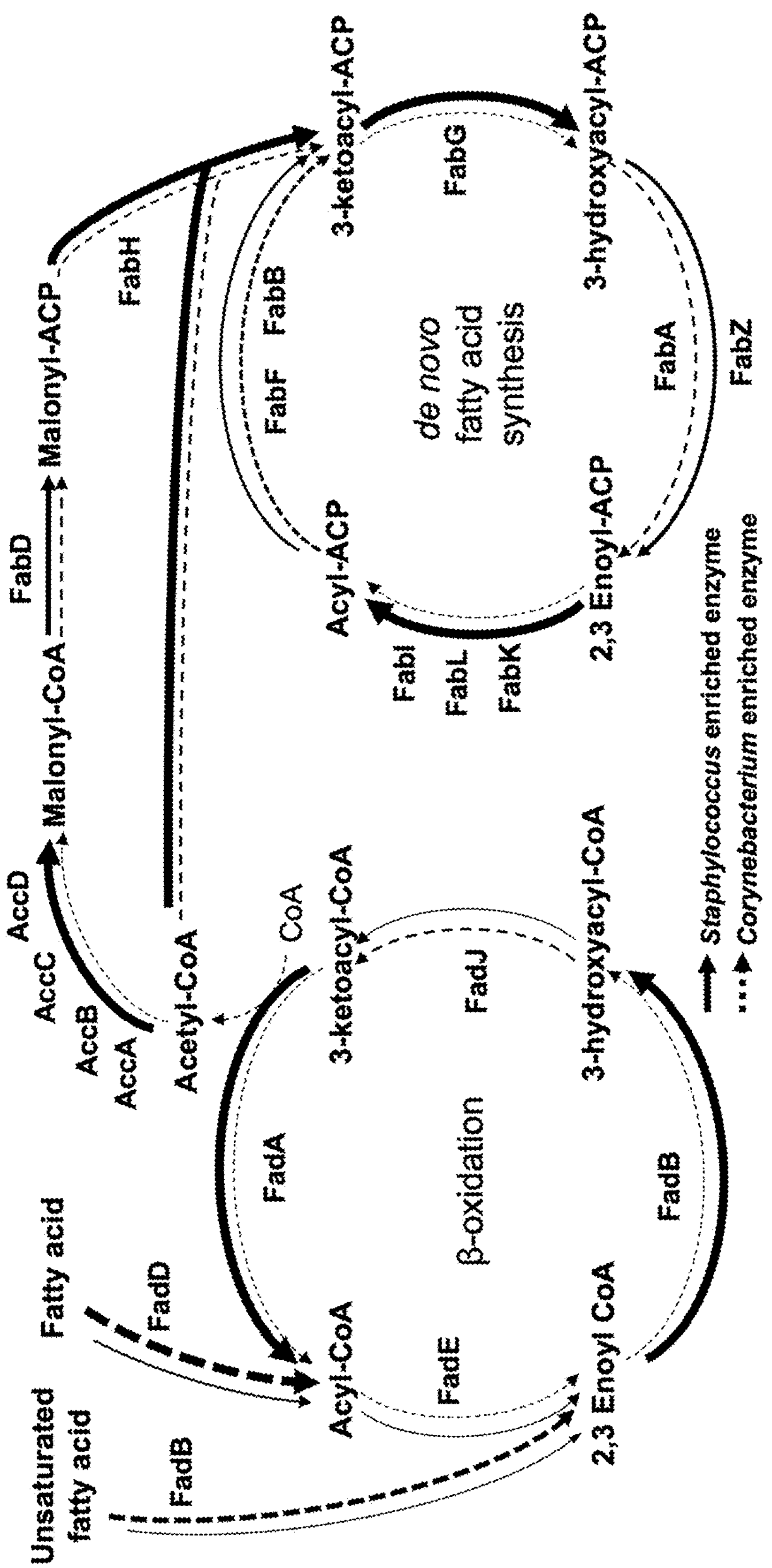
FIG. 3: Lipid degradation and biosynthesis pathways: axillary microbiomes associated with good odors show enrichment in functional composition (genes) as compared to microbiomes associated with malodor. (Unsaturated) fatty acids are easily metabolized by *Corynebacterium* in the first step, but further lack gene abundances to fully metabolize or de novo synthesis, as compared to *Staphylococcus*. Pathway of β-oxidation and fatty acid synthesis of *Staphylococcus* and *Corynebacterium* spp. are colored in full and dashed arrows, respectively.

FIG. 1 shows the enzymatic load of each bacterial group, which originates from the armpit observation study. It can be noticed that in the class of lipid metabolism enzymes *Staphylococcus epidermis* has a white color (higher enzymatic content), while *Corynebacterium* has a black color (lower enzymatic content). FIG. 2 shows a more detailed where the KEGG pathways were collapsed to level 3, for the fat-metabolizing enzymes only. Again, clear differences are seen between staphylococcal and corynebacterial enzymes for fat metabolism. In FIG. 3 finally, the lipid degradation and synthesis have been highlighted onto enzyme level. It can clearly be seen that the white lines (enzymes) are more abundant for *Staphylococcus* than for *Corynebacterium*. *Staphylococcus* is correlated with better underarm odors, while *Corynebacterium* is correlated with unpleasant body odors (fecal-like, sour, dirty, pungent, etc.). In conclusion: a higher load of lipid-degrading/catabolizing/synthetizing enzymes are needed to improve body odor.

Hence, the present disclosure describes the following enzymes that are used in the battle against body odor:

FadE (acyl CoA dehydrogenase)
FadB (enoyl CoA hydratase)
FadJ (3-hydroxyacyl-CoA dehydrogenase
FadA (β-ketothiolase)
AccA (acetyl-CoA carboxylase)
AccB (acetyl-CoA carboxylase)
AccC (acetyl-CoA carboxylase)
AccD (acetyl-CoA carboxylase)
FabD (malonyl-CoA:ACP transacylase)
FabH (β-ketoacyl-ACP synthases (initial condensation with acetyl-CoA and branched acyl-CoAs))
FabG (NADPH-dependent β-ketoacyl-ACP reductase)
FabZ (3-hydroxyacyl-ACP dehydratase)
FabA (β-hydroxydecanoyl-ACP dehydrase)
FabB (3-ketoacyl-ACP synthases I)
FabF (β-ketoacyl-ACP synthase (chain elongation))
FabI (enoyl-ACP reductase)
FabL (enoyl-ACP reductase)
FabK (enoyl-ACP reductase)
farnesyl-diphosphate farnesyltransferase
farnesyl diphosphate synthase
diphosphomevalonate decarboxylase
phosphomevalonate kinase
mevalonate kinase
hydroxymethylglutaryl-CoA reductase
hydroxymethylglutaryl-CoA synthase
acetyl-CoA C-acetyltransferase
hydroxymethylglutaryl-CoA lyase
3-oxoacid CoA-transferase
acetoacetate decarboxylase
3-hydroxybutyrate dehydrogenase
farnesyl-diphosphate
Lipases
Amylase
Protease
Cellulase The function of each of the enzymes is given hereunder:

Enzymes involved in fatty acid synthesis (see FIG. 3):

Acetyl CoA:ACP transacylase: Activates acetyl CoA for reaction with malonyl-ACP
Malonyl CoA:ACP transacylase: Activates malonyl CoA for reaction with acetyl-ACP
3-ketoacyl-ACP synthase: Reacts priming acetyl-ACP with chain-extending malonyl-ACP
3-ketoacyl-ACP reductase: Reduces the carbon 3 ketone to a hydroxyl group
3-Hydroxyacyl ACP dehydrase: Removes water
Enoyl-ACP reductase: Reduces the C2-C3 double bond.

Enzymes involved in fatty acid metabolism (beta-oxidation, see FIG. 3):

Acetyl CoA:ACP transacylase: Activates acetyl CoA for reaction with malonyl-ACP
Malonyl CoA:ACP transacylase: Activates malonyl CoA for reaction with acetyl-ACP
3-ketoacyl-ACP synthase: Reacts priming acetyl-ACP with chain-extending malonyl-ACP
3-ketoacyl-ACP reductase: Reduces the carbon 3 ketone to a hydroxyl group
3-Hydroxyacyl ACP dehydrase: Removes water
Enoyl-ACP reductase: Reduces the C2-C3 double bond.

Enzymes involved in synthesis and degradation of ketone bodies:

hydroxymethylglutaryl-CoA lyase: converts 3-hydroxy-3-methylglutaryl-coenzyme A into acetoacetate.

3-oxoacid CoA-transferase: converts acetoacetyl coenzyme A into acetoacetate.

acetoacetate decarboxylase: converts acetoacetate into acetone.

3-hydroxybutyrate dehydrogenase: converts acetoacetate into 3-hydroxybutanoate.

hydroxymethylglutaryl-CoA synthase: converts acetyl coenzyme A into 3-hydroxy-3-methylglutaryl-coenzyme A.

Figure 4:
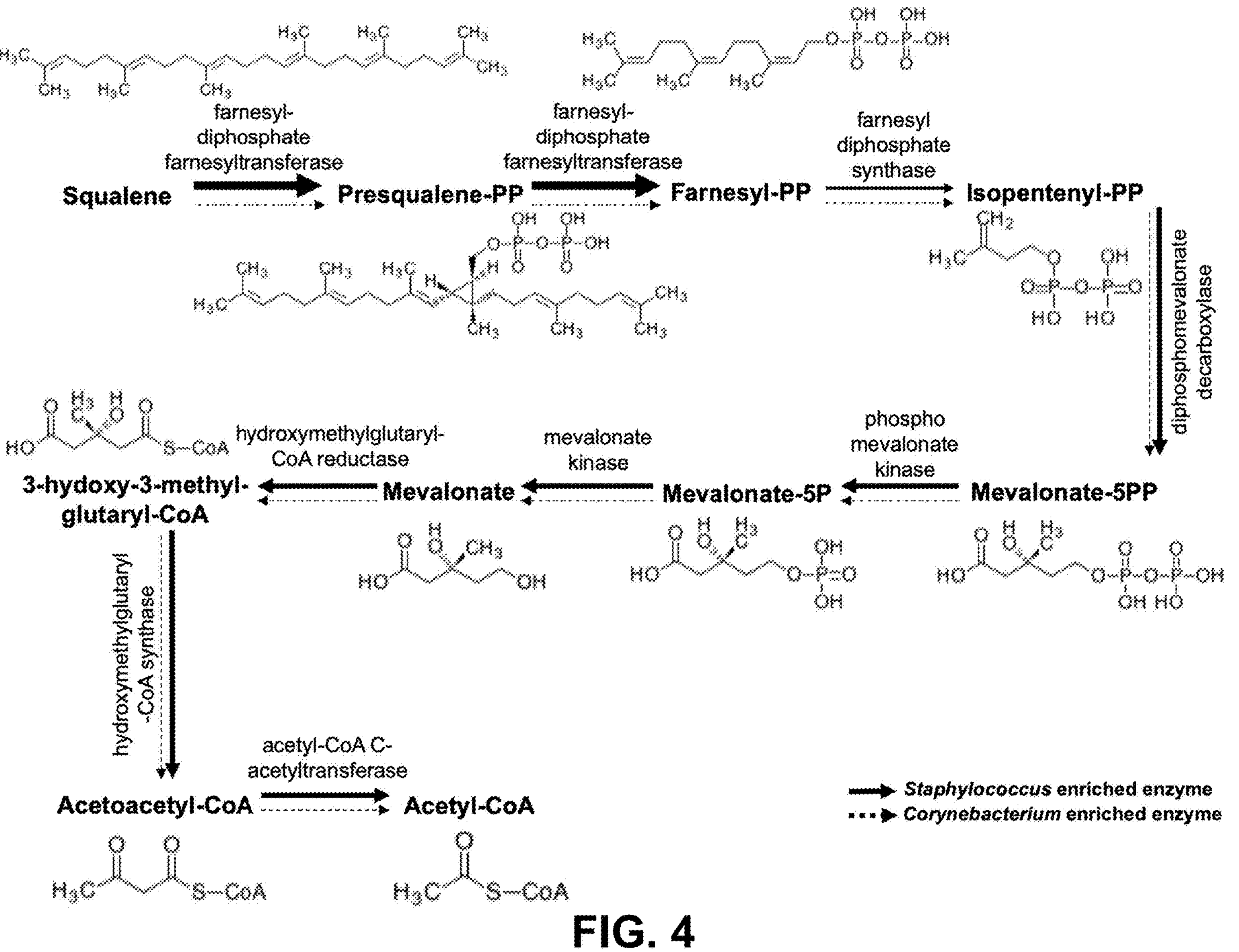
FIG. 4: Squalene degradation pathway: axillary microbiomes associated with good odors show enrichment in functional composition (genes) as compared to microbiomes associated with malodor. *Staphylococcus* spp. enzymes have more enzymes to fully degrade squalene. Squalene degradation of *Staphylococcus* and *Corynebacterium* spp. are in full and dashed arrows, respectively. Thickness of arrow indicates relative amount of enzymes present.

Enzymes involved in squalene degradation (full pathway: see FIG. 4):

- farnesyl-diphosphate farnesyltransferase: converts squalene into presqualene-diphosphate (presqualene-PP) and converts presqualene-diphosphate (presqualene-PP) into farnesyl diphosphate (farnesyl-PP)
- farnesyl diphosphate synthase: converts farnesyl diphosphate (farnesyl-PP) into isopentenyl-diphosphate (isopentenyl-PP)
- diphosphomevalonate decarboxylase: converts isopentenyl-diphosphate (isopentenyl-PP) into 5-diphosphomevalonate (mevalonate-5PP)
- phosphomevalonate kinase: converts 5-diphosphomevalonate (mevalonate-5PP) into 5-phosphomevalonate (mevalonate-5P)
- mevalonate kinase: converts 5-phosphomevalonate (mevalonate-5P) into mevalonate
- hydroxymethylglutaryl-CoA reductase: converts mevalonate into 3-hydroxy-3-methyl-glutaryl coenzyme A.
- hydroxymethylglutaryl-CoA synthase: converts 3-hydroxy-3-methyl-glutaryl coenzyme A into acetoacetyl coenzyme A.
- acetyl-CoA C-acetyltransferase: converts acetoacetyl coenzyme A into acetyl coenzyme A.

Enzyme involved in production of farnesol or farnesal, a natural fragrance:

- farnesyl diphosphatase: converts farnesyl-diphosphate (breakdown product of squalene) to farnesol
- production of a natural fragrance from squalene breakdown compounds.

This enzyme is present in *Saccharomyces cerevisiae*

Function of lipase, amylase, protease, cellulase:

Breakdown of carbohydrate, proteolytic or fatty matrix compounds the sweat precipitations.

A more thorough review on the bacterial enzymes as described above can be found with Fujita et al. (2007) (35).

2.2 Spray with Lyophilized Bacteria

Figure 5:
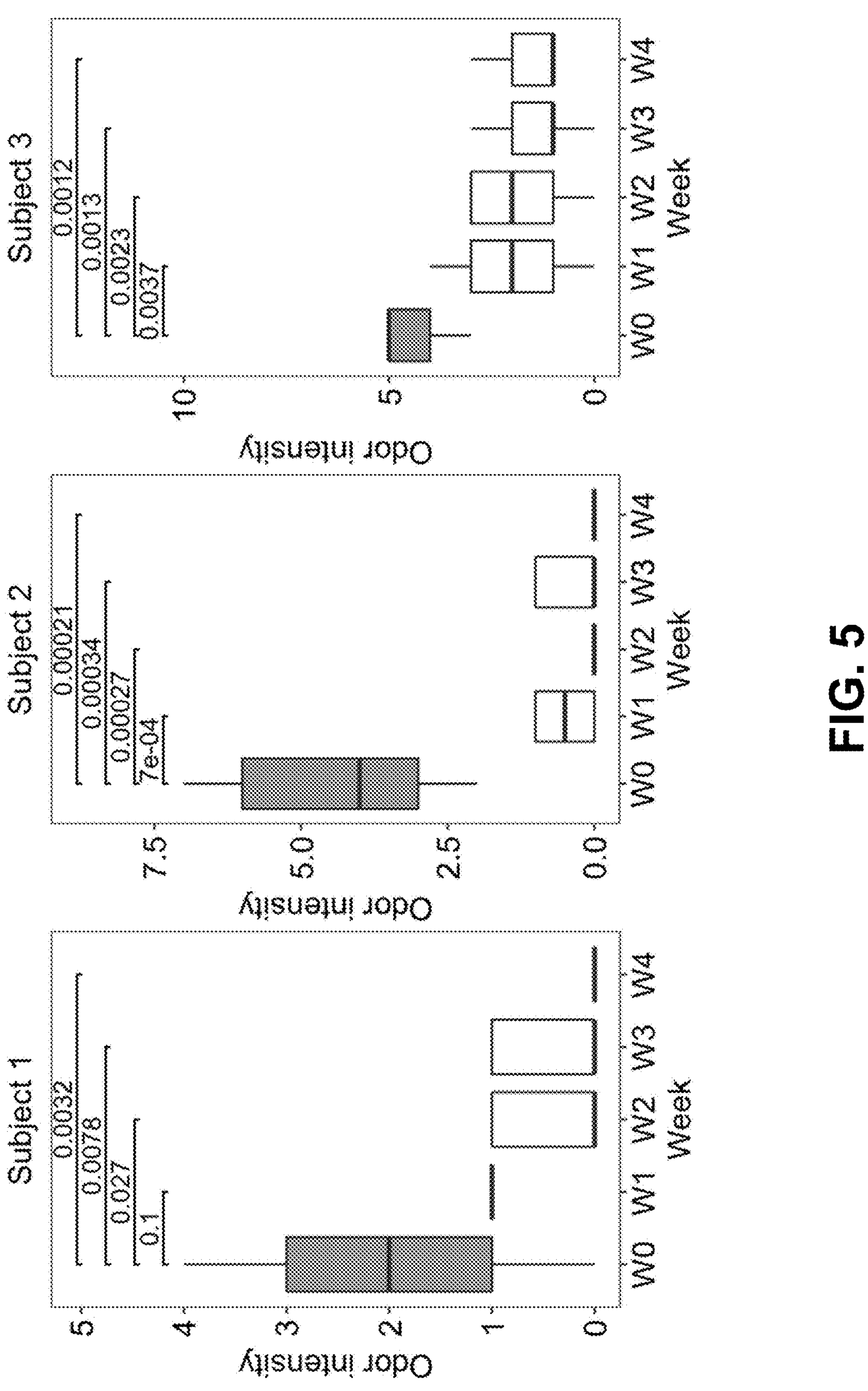
FIG. 5: Subjects with bromhidrosis treated with lyophilized *Staphylococcus* bacteria. Odor panel verified the odor intensity on five consecutive weeks. The first week (week 0—W0) was status without treatment (grey boxplot), while the last four weeks (week 1 W1, week 2 W2, week 3 W3, week 4 W4) was during treatment (white boxplots). The lyophilized viable bacteria were tested on three different subjects and showed a significant decrease in underarm odor intensity upon use of the spray containing the bacterial lysates. Differences in odor intensity were assessed using the Mann-Whitney U-test; values shown on top of the plots.

Three subjects with above-average malodorous axillae were selected, as determined by the odor panel. The subjects used the lyophilized bacterial spray on a daily basis during four consecutive weeks. In the week preceding the treatment, no bacteria were applied in the underarms. The subjects wore a cotton pad in the underarm to capture the odor, after which the sample was frozen until odor assessment by the trained odor panel. The subjects self-assessed the underarm odor and marked significant improvements during the use of the spray. The improved odor was also reported on clothing and elsewhere on the skin when the bacterial spray was applied. The trained and selected odor panel reported a significant decrease (as determined by the Mann-Whitney U-test; $p<0.05$) in underarm intensity when the bacteria were applied, as compared to when no bacteria were applied (FIG. 5).

2.3 Spray with Bacterial Enzymes

Figure 6:
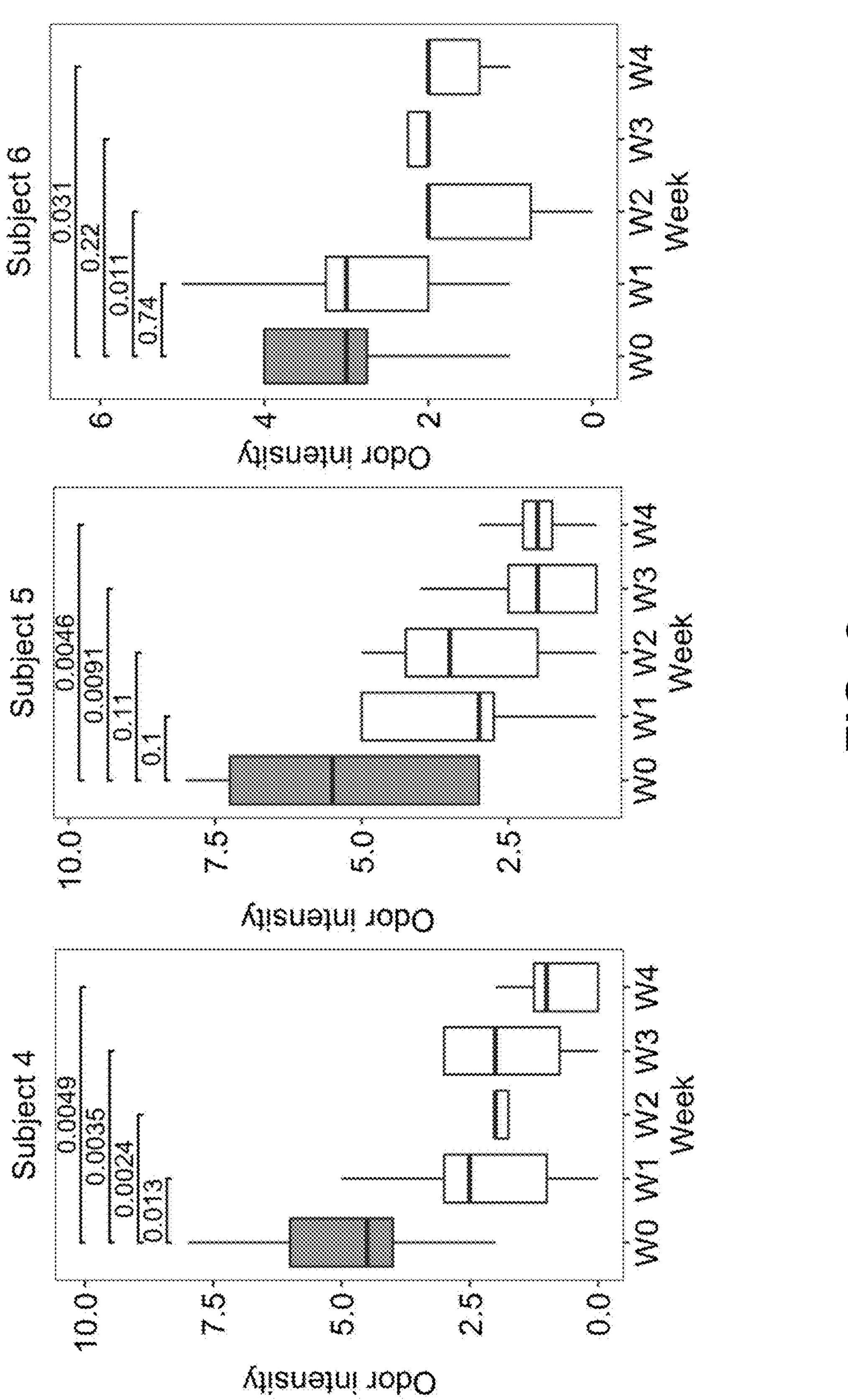
FIG. 6: Subjects with bromhidrosis treated with *Staphylococcus* lysates containing the active enzymes, as verified by the enzymatic assay. Odor panel verified the odor intensity, on five consecutive weeks. The first week (week 0—W0) was status without treatment (grey boxplot), while the last four weeks (week 1 W1, week 2 W2, week 3 W3, week 4 W4) was during treatment (white boxplots). The bacterial lysates were tested on three different subjects and showed a significant decrease in underarm odor intensity upon use of the spray containing the bacterial lysates. Differences in odor intensity were assessed using the Mann-Whitney U-test; values shown on top of the plots.

Three subjects with above-average malodorous axillae, as determined by the odor panel, were selected for the bacterial enzyme spray. It was confirmed that the bacterial lysates had active enzymatic activity and no viable bacterial cells. The subjects used the enzyme spray on a daily basis during four consecutive weeks. In the week preceding the treatment, no enzymes were applied in the underarms. The subjects wore a cotton pad in the underarm to capture the odor during five consecutive weeks, after which the sample was frozen until odor assessment by the trained odor panel. The subjects self-assessed the underarm odor and marked significant improvements during the use of the enzymes. Participants also reported a decreased body on clothing and elsewhere on the skin when the enzymes were applied. The trained and selected odor panel reported a significant decrease (as determined by the Mann-Whitney U-test; $p<0.05$) in underarm intensity when the enzymes were applied, as compared to when no enzymes were applied (FIG. 6).

REFERENCES

1. Grice E. A., Kong H. H., Renaud G., Young A. C., Bouffard G. G., Blakesley R. W., et al. A diversity profile of the human skin microbiota. Genome Res. 2008; 18(7): 1043-50.
2. Troccaz M., Gaïa N., Beccucci S., Schrenzel J., Cayeux I., Starkenmann C., et al. Mapping axillary microbiota responsible for body odors using a culture-independent approach. Microbiome 2015; 3(1):1-15.
3. Callewaert C., Lambert J., Van de Wiele T. Towards a bacterial treatment for armpit malodor. Exp. Dermatol. 2016 Nov. 28 [cited 2017 Jan. 6]*; Experimental dermatology* 26.5 (2017): 388-391.
4. Lillis P. J., Coleman W. P. Liposuction for treatment of axillary hyperhidrosis. Dermatol. Clin. 1990; 8(3):479-82.
5. Heckmann M., Ceballos-Baumann A. O., Plewig G. Hyperhidrosis Study G. Botulinum toxin a for axillary hyperhidrosis (excessive sweating). N. Engl. J. Med. 2001; 344(7):488-93.
6. Tung T. C., Wei F. C. Excision of subcutaneous tissue for the treatment of axillary osmidrosis. Br. J. Plast. Surg. 1997; 50(1):61-6.
7. Kim I. H., Seo S. L., Oh C. H. Minimally invasive surgery for axillary osmidrosis: combined operation with CO2 laser and subcutaneous tissue remover. Dermatologic Surg [Internet]. 1999; 25(11):875-9. dx.doi.org/10.1046/j.1524-4725.1999.99116.x.
8. Lee S.-J., Chang K.-Y., Suh D.-H., Song K.-Y., Ryu H. J. The efficacy of a microwave device for treating axillary hyperhidrosis and osmidrosis in Asians: a preliminary study. J. Cosmet. Laser Ther. 2013; 15(5):255-9.
9. Begum M., McKenna P. J. Olfactory reference syndrome: a systematic review of the world literature. Psychol. Med. 2011; 41(3):453-61.
10. Soriano F., Zapardiel J., Nieto E. Antimicrobial susceptibilities of *Corynebacterium* species and other non-spore-forming gram-positive bacilli to 18 antimicrobial agents. Antimicrob. Agents Chemother. 1995; 39(1):208-14.
11. Makin S. A., Lowry M. R. Deodorant Ingredients. In: K. Laden, editor Antiperspirants and deodorants. New York: Marcel Dekker; 1999. p. 169-214.
12. Boonme P., Songkro S. Antiperspirants and Deodorants: Active Ingredients and. 2010; (01):5-10.

13. Callewaert C., Hutapea P., Van de Wiele T., Boon N. Deodorants and antiperspirants affect the axillary bacterial community. Arch. Dermatol. Res. 2014 Sep. 19; 306(8):701-10.

14. Bouslimani A., Silva R., Amir A., Kosciolek T., Janssen S., Dorrestein K., et al. Modifying skin metabolome and microbiome with personal care products. Manuscript in preparation. 2017;

15. Casey J., Ellis J. E., James A. G., Taylor G. M. Method of reducing or preventing malodor. WO2000001353A1, 1998. p. 1-25.

16. Brockett Lyon S., O'Neal C., Van Der Lee H., Rogers B. Amino acid beta-lyase enzyme inhibitors as deodorants WO1991005541A1, 1990. p. 1-16.

17. Austin C. J., Casey J., Ellis J. E. Method of reducing or preventing malodor. WIPO (PCT); WO2000001355A1, 1998. p. 1-21.

18. Acuna G., Gfeller H., Natsch A. Compounds and methods for inhibiting axillary malodor. European Patent Office; EP1258531A1, 2001. p. 1-24.

19. Bawdon D., Cox D. S., Ashford D., James A. G., Thomas G. H. Identification of axillary *Staphylococcus* sp. involved in the production of the malodorous thioalcohol 3-methyl-3-sufanylhexan-1-ol. FEMS Microbiol. Lett. 2015/07/15. 2015; 362(16).

20. Dewolf W. E. J., Kallender H., Lonsdale J. T. High throughput screening method for biological agents affecting fatty acid biosynthesis. USA; U.S. Pat. No. 6,951, 729B1, 2000. p. 1-53.

21. Nicolaides N. Skin lipids—Their biochemical uniqueness. Science (80-). 1974; 186(4158):19-26.

22. Tauch A., Kaiser O., Hain T., Goesmann A., Weisshaar B., Albersmeier A., et al. Complete genome sequence and analysis of the multiresistant nosocomial pathogen *Corynebacterium jeikeium* K411, a lipid-requiring bacterium of the human skin flora. J. Bacteriol. 2005 July; 187(13):4671-82.

23. Barzantny H., Brune I., Tauch A. Molecular basis of human body odor formation: insights deduced from corynebacterial genome sequences. Int. J. Cosmet. Sci. 2012; 34(1):2-11.

24. Barzantny H., Guttmann S., Lassig C., Brune I., Tauch A. Transcriptional control of lipid metabolism by the MarR-like regulator FamR and the global regulator GlxR in the lipophilic axilla isolate *Corynebacterium jeikeium* K411. Microb. Biotechnol. 2013 March; 6(2): 118-30.

25. Decréau R. A., Marson C. M., Smith K. E., Behan J. M. Production of malodorous steroids from androsta-5,16-dienes and androsta-4,16-dienes by Corynebacteria and other human axillary bacteria. J. Steroid Biochem. Mol. Biol. 2003; 87:327-36.

26. Heckly R. J. Preservation of Microorganisms. In: Perlman DBT-A in AM, editor. Academic Press; 1978. p. 1-53. sciencedirect.com/science/article/pii/S006521640870635X.

27. Nicolaides N., Kellum R. E., Woolley P. V. 3rd. The Structures of the Free Unsaturated Fatty Acids of Human Skin Surface Fat. Arch. Biochem. Biophys. 1964 June; 105:634-9.

28. Nicolaides N., Apon J. M. B. The saturated methyl branched fatty acids of adult human skin surface lipid. Biomed. Mass Spectrom. 1977 Dec. 1; 4(6):337-47.

29. Zeng X. N., Leyden J. J., Lawley H. J., Sawano K., Nohara I., Preti G. Analysis of characteristic odors from human male axillae. J. Chem. Ecol. 1991; 17(7):1469-92.

30. Natsch A., Gfeller H., Gygax P., Schmid J., Acuna G. A specific bacterial aminoacylase cleaves odorant precursors secreted in the human axilla. J. Biol. Chem. 2003; 278(8):5718-27.

31. Natsch A., Derrer S., Flachsmann F., Schmid J. A broad diversity of volatile carboxylic acids, released by a bacterial aminoacylase from axilla secretions, as candidate molecules for the determination of human-body odor type. Chem. Biodivers. 2006; 3(1):1-20.

32. Labows J. N., Preti G., Hoelzle E., Leyden J., Kligman A. Steroid analysis of human apocrine secretion. Steroids. 1979/09/01. 1979; 34(3):249-58.

33. Takeuchi K., Yabuki M., Hasegawa Y. Review of odorants in human axillary odor and laundry malodor: The importance of branched C7 chain analogues in malodors perceived by humans. Flavor Fragr. J. 2012 Nov. 28; 28(4):223-30.

34. Martin A., Saathoff M., Kuhn F., Max H., Terstegen L., Natsch A. A functional ABCC11 allele is essential in the biochemical formation of human axillary odor. J. Invest. Dermatol. 2010 February; 130(2):529-40.

35. Fujita Y., Matsuoka H., Hirooka K. Regulation of fatty acid metabolism in bacteria. Molecular Microbiology. 2007.

36. James A. G., Casey J., Hyliands D., Mycock G. Fatty acid metabolism by cutaneous bacteria and its role in axillary malodor. World J. Microbiol. Biotechnol. 2004; 20(8):787-93.

37. James A. G., Austin C. J., Cox D. S., Taylor D., Calvert R. Microbiological and biochemical origins of human axillary odor. FEMS Microbiol. Ecol. 2013; 83(3):527-40.

38. Natsch A., Schmid J., Flachsmann F. Identification of odoriferous sulfanylalkanols in human axilla secretions and their formation through cleavage of cysteine precursors by a C-S lyase isolated from axilla bacteria. Chem. Biodivers. 2004; 1(7):1058-72.

39. Hasegawa Y., Yabuki M., Matsukane M. Identification of new odoriferous compounds in human axillary sweat. Chem. Biodivers. 2004; 1(12):2042-50.

40. Troccaz M., Starkenmann C., Niclass Y., van de Waal M., Clark A. J. 3-methyl-3-sulfanylhexan-1-ol as a major descriptor for the human axilla-sweat odor profile. Chem. Biodivers. 2004; 1(7):1022-35.

41. Chen Z.-S., Guo Y., Belinsky M. G., Kotova E., Kruh G. D. Transport of bile acids, sulfated steroids, estradiol 17-beta-D-glucuronide, and leukotriene C4 by human multidrug resistance protein 8 (ABCC11). Mol. Pharmacol. 2005 February; 67(2):545-57.

42. Evans C. A., Stevens R. J. Differential quantitation of surface and subsurface bacteria of normal skin by combined use of cotton swab and scrub methods. J. Clin. Microbiol. 1976; 3(6): 576-81.

43. Callewaert C., De Maeseneire E., Van de Wiele T., Boon N. Bacterial and odor profile of polyester and cotton clothes after a fitness session. Commun. Agric. Appl. Biol. Sci. 2013; 78(1).

44. Amoore J. E., Venstrom D., Nutting M. D. Sweaty odor in fatty acids—Measurements of similarity, confusion and fatigue. J. Food Sci. 1972; 37(1):33-5.

45. Rodriguez-Lazaro D., Jofre A., Aymerich T., Hugas M., Pla M. Rapid quantitative detection of *Listeria monocytogenes* in meat products by real-time PCR. Appl. Environ. Microbiol. 2004; 70(10):6299-301.

46. Juste A., Thomma B. P. H. J., Lievens B. Recent advances in molecular techniques to study microbial communities in food-associated matrices and processes. Food Microbiol. 2008; 25(6):745-61.

47. Chakravorty S., Helb D., Burday M., Connell N. A detailed analysis of 16S ribosomal RNA gene segments for the diagnosis of pathogenic bacteria. J. Microbiol. Methods. 2007; 69(2):330-9.

48. Camarinha-Silva A., Jauregui R., Chaves-Moreno D., Oxley A. P., Schaumburg F., Becker K., et al. Comparing the anterior nare bacterial community of two discrete human populations using Illumina amplicon sequencing. Environ. Microbiol. 2013/12/21. 2014; 16(9):2939-52.

49. Hamady M., Walker J. J., Harris J. K., Gold N. J., Knight R. Error-correcting barcoded primers for pyrosequencing hundreds of samples in multiplex. Nat. Methods. 2008; 5(3):235-7.

50. McDonald D., Price M. N., Goodrich J., Nawrocki E. P., DeSantis T. Z., Probst A., et al. An improved Greengenes taxonomy with explicit ranks for ecological and evolutionary analyses of bacteria and archaea. ISME J. 2012; 6(3):610-8.

51. Edgar R. C. Search and clustering orders of magnitude faster than BLAST. Bioinformatics. 2010; 26(19):2460-1.

52. Caporaso J. G., Kuczynski J., Stombaugh J., Bittinger K., Bushman F. D., Costello E. K., et al. QIIME allows analysis of high-throughput community sequencing data. Vol. 7, Nature methods. United States; 2010. p. 335-6.

53. Weiss S. J., Xu Z., Amir A., Peddada S., Bittinger K., Gonzalez A., et al. Effects of library size variance, sparsity, and compositionality on the analysis of microbiome data. Peer J. Prepr. 2015; 3:e1408.

54. Langille M. G. I., Zaneveld J., Caporaso J. G., McDonald D., Knights D., Reyes J. A., et al. Predictive functional profiling of microbial communities using 16S rRNA marker gene sequences. Nat. Biotechnol. 2013 September; 31(9):814-21.

55. Kanehisa M., Goto S., Sato Y., Furumichi M., Tanabe M. KEGG for integration and interpretation of large-scale molecular data sets. Nucleic Acids Res. 2012 January; 40 (Database issue):D109-14.

56. Joyce E., Al-Hashimi A., Mason T. J. Assessing the effect of different ultrasonic frequencies on bacterial viability using flow cytometry. J. Appl. Microbiol. 2011 April; 110(4): 862-70.

57. Özbek B., Ulgen K. O. The stability of enzymes after sonication. Process Biochem. 2000; 35(9):1037-43. sciencedirect.com/science/article/pii/S0032959200001412.

58. Duong-Ly K. C., Gabelli S. B. Salting out of proteins using ammonium sulfate precipitation. Methods Enzymol. 2014; 541:85-94.

59. Lawrence R. C., Fryer T. F., Reiter B. Rapid Method for the Quantitative Estimation of Microbial. Lipases. Nature 1967; 213(5082):1264-5.

60. Samad M. Y. A., Razak C. N. A., Salleh A. B., Zin Wan Yunus W. M., Ampon K., Basri M. A plate assay for primary screening of lipase activity. J. Microbiol. Methods [Internet]. 1989; 9(1):51-6. 0167701289900304.

61. Callewaert C., Buysschaert B., Vossen E., Fievez V., Van de Wiele T., Boon N. Artificial sweat composition to grow and sustain a mixed human axillary microbiome. J. Microbiol. Methods. 2014; 103:6-8.

The invention claimed is:

1. A method of reducing the amount of malodorous fatty acids in a subject's sweat by fatty acid and/or squalene breakdown, the method comprising:

obtaining by purification a mix of isolated functional enzymes from a bacterial *Staphylococcus* species; and applying the mix of isolated functional enzymes topically, wherein the mix of isolated functional enzymes catabolizes human skin lipids and/or squalene, so as to reduce the amount of malodorous fatty acids in the subject's sweat.

2. The method according to claim 1, wherein the mix of isolated functional enzymes comprises acyl CoA dehydrogenase FadE, enoyl CoA hydratase FadB, 3-hydroxyacyl-CoA dehydrogenase FadJ, and β-ketothiolase FadA.

3. The method according to claim 1, wherein the mix of isolated functional enzymes comprises acetyl-CoA carboxylase AccA, acetyl-CoA carboxylase AccB, acetyl-CoA carboxylase AccC, acetyl-CoA carboxylase AccD, malonyl-CoA:ACP transacylase FabD, β-ketoacyl-ACP synthases FabH, NADPH-dependent β-ketoacyl-ACP reductase FabG, 3-hydroxyacyl-ACP dehydratase FabZ, β-hydroxydecanoyl-ACP dehydrase FabA, 3-ketoacyl-ACP synthases I FabB, β-ketoacyl-ACP synthase FabF, enoyl-ACP reductase FabI, enoyl-ACP reductase FabL, and enoyl-ACP reductase FabK.

4. The method according to claim 1, wherein the mix of isolated functional enzymes comprises acetyl-CoA C-acetyltransferase, hydroxymethylglutaryl-CoA synthase, hydroxymethylglutaryl-CoA lyase, 3-oxoacid CoA-transferase, acetoacetate decarboxylase, and 3-hydroxybutyrate dehydrogenase.

5. The method according to claim 1, wherein the mix of isolated functional enzymes comprises farnesyl-diphosphate farnesyltransferase, farnesyl diphosphate synthase, diphosphomevalonate decarboxylase, phosphomevalonate kinase, mevalonate kinase, hydroxymethylglutaryl-CoA reductase, hydroxymethylglutaryl-CoA synthase, and acetyl-CoA C-acetyltransferase.

6. The method according to claim 1, wherein the subject's sweat is present on skin and/or on a textile.

7. The method according to claim 1, wherein the mix of isolated functional enzymes is incorporated into a spray, deodorant, washing powder, or clothing finishing agent.

8. The method according to claim 1, wherein the mix of isolated functional enzymes reduces body odor of the subject.

9. The method according to claim 1, wherein the mix of isolated functional enzymes is incorporated into a deodorant or antiperspirant.

10. The method according to claim 1, wherein the mix of isolated functional enzymes comprises acyl CoA dehydrogenase FadE, enoyl CoA hydratase FadB, 3-hydroxyacyl-CoA dehydrogenase FadJ, β-ketothiolase FadA, acetyl-CoA carboxylase AccA, acetyl-CoA carboxylase AccB, acetyl-CoA carboxylase AccC, acetyl-CoA carboxylase AccD, malonyl-CoA:ACP transacylase FabD, β-ketoacyl-ACP synthases FabH, NADPH-dependent β-ketoacyl-ACP reductase FabG, 3-hydroxyacyl-ACP dehydratase FabZ, β-hydroxydecanoyl-ACP dehydrase FabA, 3-ketoacyl-ACP synthases I FabB, β-ketoacyl-ACP synthase FabF, enoyl-ACP reductase FabI, enoyl-ACP reductase FabL, enoyl-ACP reductase FabK, hydroxymethylglutaryl-CoA synthase, hydroxymethylglutaryl-CoA lyase, 3-oxoacid CoA-transferase, acetoacetate decarboxylase, 3-hydroxybutyrate dehydrogenase, farnesyl-diphosphate farnesyltransferase, farnesyl diphosphate synthase, diphosphomevalonate decarboxylase, phosphomevalonate kinase, mevalonate kinase, hydroxymethylglutaryl-CoA reductase, and acetyl-CoA C-acetyltransferase.

11. The method according to claim 1, wherein the purification of the mix of isolated functional enzymes from the bacterial *Staphylococcus* species comprises: sonication to disrupt bacterial *Staphylococcus* cells, centrifugation to separate large particles from the functional enzymes, bringing the functional enzymes into solution, and purification and precipitation of the functional enzymes using ammonium sulfate and crystallization by changing the pH.

* * * * *